(12) United States Patent
Kwak et al.

(10) Patent No.: US 9,474,504 B2
(45) Date of Patent: Oct. 25, 2016

(54) METHOD AND APPARATUS FOR OBTAINING TISSUE DOPPLER IMAGES

(71) Applicant: SAMSUNG MEDISON CO., LTD., Gangwon-do (KR)

(72) Inventors: Han Kwak, Gangwon-do (KR);
Jae-keun Lee, Gangwon-do (KR);
Hyeong-do Lee, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 239 days.

(21) Appl. No.: 13/707,319

(22) Filed: Dec. 6, 2012

(65) Prior Publication Data

US 2013/0253320 A1    Sep. 26, 2013

(30) Foreign Application Priority Data

Mar. 23, 2012  (KR) .................. 10-2012-0030032

(51) Int. Cl.
*A61B 8/14*    (2006.01)
*A61B 8/08*    (2006.01)

(52) U.S. Cl.
CPC .............. *A61B 8/14* (2013.01); *A61B 8/488* (2013.01); *A61B 8/5207* (2013.01)

(58) Field of Classification Search
None
See application file for complete search history.

(56) References Cited

U.S. PATENT DOCUMENTS

| | | | |
|---|---|---|---|
| 5,170,792 A * | 12/1992 | Sturgill et al. | 600/455 |
| 5,718,229 A * | 2/1998 | Pesque et al. | 600/441 |
| 6,419,632 B1 * | 7/2002 | Shiki et al. | 600/443 |
| 7,347,820 B2 | 3/2008 | Bonnefous | |
| 8,157,734 B2 | 4/2012 | Nakata | |
| 8,614,635 B2 * | 12/2013 | Hode | 341/118 |
| 2011/0263985 A1 | 10/2011 | Gauthier et al. | |

FOREIGN PATENT DOCUMENTS

| | | |
|---|---|---|
| JP | 2000-342586 A | 12/2000 |
| JP | 2006-505321 A | 2/2006 |
| JP | 2006-116149 A | 5/2006 |
| JP | 2010-537698 A | 12/2010 |

OTHER PUBLICATIONS

Korean Notice of Allowance issued in Korean Application No. 10-2012-0030032 dated Apr. 24, 2014, w/English translation.
Korean Office Action issued in Korean Application No. 10-2012-0030032 dated Feb. 26, 2014, w/English translation.
Korean Office Action, w/ English translation thereof, issued in Korean Patent Application No. KR 10-2012-0030032 dated Aug. 26, 2013.

* cited by examiner

*Primary Examiner* — Long V Le
*Assistant Examiner* — Kevin Pontius
(74) *Attorney, Agent, or Firm* — McDermott Will & Emery LLP (57) ABSTRACT

A method of obtaining a Doppler image of tissue which is captured using an ultrasonic wave. The method includes: transmitting an ultrasonic signal to a target object such that a plurality of ensembles are formed and receiving an ultrasonic response signal from the target object. The method further includes filtering the received ultrasonic response signal by using a variable filter and estimating a frequency of the received ultrasonic response signal based on the filtered data. Thereafter, the Doppler image of the tissue based on the estimated frequency can be generated.

7 Claims, 7 Drawing Sheets

METHOD AND APPARATUS FOR OBTAINING TISSUE DOPPLER IMAGES

CROSS-REFERENCE TO RELATED PATENT APPLICATION

This application claims the benefit of Korean Patent Application No. 10-2012-0030032, filed on Mar. 23, 2012, in the Korean Intellectual Property Office, the disclosure of which is incorporated herein in its entirety by reference.

BACKGROUND OF THE INVENTION

1. Field of the Invention

The present invention relates to tissue Doppler imaging (TDI), and more particularly, to a method and apparatus for obtaining Doppler images of tissue, which are captured using ultrasonic waves.

2. Description of the Related Art

An ultrasonic system is non-invasive and non-destructive, and thus is widely used in the medical field for obtaining information about the inside of a target object. An ultrasonic system provides high-resolution images of tissue inside a human body to medical doctors in real-time without the need of a surgical operation including direct incision and observation of the human body, and thus is used as an important device in the medical field.

An ultrasonic diagnosis apparatus transfers an ultrasonic wave signal from a body surface of a target object toward a predetermined portion in a body to obtain an image about a cross-section or hematoceles of soft tissue using information of the ultrasonic signal that is reflected by the tissue inside the body.

The ultrasonic diagnosis apparatus is compact, inexpensive, and is displayable in real-time. In addition, the ultrasonic diagnosis apparatus does not cause exposure to radiation, for example, X-rays, and is thus stable, and is widely used with other imaging diagnosis apparatuses such as an X-ray diagnosis apparatus, a computerized tomography (CT) scanner, a magnetic resonance imaging apparatus, or a nuclear medical diagnosis apparatus. Also, the ultrasonic diagnosis apparatus provides high-resolution images of the inside of a target object to medical doctors in real-time without a surgical operation including direct incision and observation of the target object, and thus is used as an important device in the medical field.

Hematoceles and myocardium react differently to ultrasonic waves. That is, hematoceles move far faster than myocardium but weakly reflect an ultrasonic wave. However, myocardium move slower than hematoceles but more strongly reflect an ultrasonic wave. Thus, when an ultrasonic signal reflected by hematoceles is removed from an ultrasonic response signal using these different characteristics, velocity of myocardial tissue may be measured. Evaluation of states of myocardium using the measured velocity of myocardial tissue refers to tissue Doppler imaging (TDI).

According to TDI, an identical sound field is transmitted to a scan line at predetermined time intervals to sense a variation in a phase of a received ultrasonic wave, and an average Doppler frequency is searched for simply by using auto-correlation, and a target object is displayed in a color image. Through the TDI, movement velocities of heart walls of a systolic period and a relaxation period may be objectively evaluated, and functional disorders of a heart may be examined for each portion of the heart, and a myocardium velocity may be quantitatively evaluated. Thus, TDI is very useful in tracking observation of a heart function regarding congenital and acquired heart diseases.

SUMMARY OF THE INVENTION

The present invention provides a method and apparatus for obtaining Doppler images of tissues captured using an ultrasonic wave.

According to an aspect of the present invention, there is provided a method of obtaining a Doppler image of tissue, which is captured using an ultrasonic wave, the method including: transmitting an ultrasonic signal to a target object such that a plurality of ensembles are formed; receiving an ultrasonic response signal from the target object; filtering the received ultrasonic response signal by using a variable filter; estimating a frequency of the received ultrasonic response signal based on the filtered data; and generating the Doppler image of the tissue based on the estimated frequency.

The plurality of ensembles may comprise at least two ensembles.

The variable filter may include a filter for removing a portion of a direct current (DC) component from the received ultrasonic response signal.

The filtering of the received ultrasonic response signal may comprise obtaining at least one of data about a filtered amplitude of the received ultrasonic response signal and data about a filtered phase of the received ultrasonic response signal.

The estimating of the frequency of the received ultrasonic response signal may further comprise obtaining a frequency phase response curve of a variable filter and correcting data about a filtered phase by using a value on the frequency phase response curve of the variable filter corresponding to the data about a filtered phase.

The generating of the Doppler image of the tissue based on the estimated frequency may comprise obtaining an amplitude of the received ultrasonic response signal and generating the Doppler image of the tissue based on the estimated frequency and the obtained amplitude.

According to another aspect of the present invention, there is provided an apparatus for obtaining a Doppler image of tissue, which is captured using an ultrasonic signal. The apparatus may comprise a transmitting unit transmitting an ultrasonic signal to an target object such that a plurality of ensembles are formed, a receiving unit receiving an ultrasonic response signal from the target object, a signal processing unit processing the received ultrasonic response signal and an image processing unit generating the Doppler image of the tissue using the processed ultrasonic response signal.

The signal processing unit may comprise a variable filter unit filtering the received ultrasonic response signal and a frequency estimating unit estimating a frequency of the received ultrasonic response signal based on the filtered data.

The plurality of ensembles may comprise at least two ensembles.

The variable filter unit may include a filter for removing a portion of a direct current (DC) component from the received ultrasonic response signal.

The variable filter unit may obtain at least one of data about a filtered amplitude of the received ultrasonic response signal and data about a filtered phase of the received ultrasonic response signal.

The frequency estimating unit may comprise a frequency analyzing unit obtaining a frequency phase response curve from the variable filter unit and a frequency compensating unit compensating for data about the filtered phase by using the obtained frequency phase response curve of the variable filter unit.

The frequency compensating unit may correct data about the filtered phase by using a value on the frequency phase response curve of the variable filter corresponding to the data about the filtered phase.

The image processing unit may comprise an amplitude detecting unit obtaining an amplitude of the received ultrasonic response signal and an image generating unit generating the Doppler image of the tissue based on the estimated frequency and the obtained amplitude.

According to another aspect of the present invention, there is provided a computer-readable recording medium having embodied thereon a computer program for executing the above-mentioned method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the terms used in the specification will be briefly described, and then the present invention will be described in detail.

The terms used in this specification are those general terms currently widely used in the art in consideration of functions in regard to the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

Throughout the specification, it will also be understood that when a component "includes" an element, unless there is another opposite description thereto, it should be understood that the component does not exclude another element but may further include another element. In addition, terms such as " . . . unit", " . . . module", or the like refer to units that perform at least one function or operation, and the units may be implemented as hardware or software or as a combination of hardware and software.

Throughout the specification, an "ultrasonic image" refers to an image of a target object obtained using an ultrasonic wave. The target object may refer to a portion of a body. For example, the target object may be an organ such as a liver, heart, uterus, brain, breast, or stomach, or may be an embryo.

Throughout the specification, a "user" may refer to a medical specialist such as a doctor, nursing staff, a clinical pathologist, or a medical imaging specialist, but is not limited thereto.

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those of ordinary skill in the art. Like numbers refer to like elements throughout.

Expressions such as "at least one of," when preceding a list of elements, modify the entire list of elements and do not modify the individual elements of the list.

A "Doppler mode" used in the embodiments of the present invention include a continuous wave (CW) mode, a pulsed wave (PW) method, a single gate method, a multi-gate method, a color flow imaging method, etc.

An ultrasonic diagnosis apparatus may provide color Doppler mode images displaying movements of a target object and a diffuser, by using the Doppler effects. A color Doppler mode image includes a power mode image showing power of a Doppler signal in a two-dimensional distribution and a velocity mode image showing an average frequency (velocity) of a Doppler signal in a two-dimensional distribution. A color Doppler mode image may visualize in real-time a moving target object.

In general, a color Doppler mode image is formed by performing clutter filtering on a Doppler signal using a filtering unit having a predetermined cutoff frequency and then using the Doppler signal on which the clutter filtering is performed.

Also, the ultrasonic system provides a B-mode in which a reflection coefficient of an ultrasonic signal reflected by a target object is shown in two dimensions, a Doppler mode in which an image of a target object (particularly, hematoceles) that moves using the Doppler effects is displayed, and an elastic mode in which a difference in reactions when a target object is compressed and not compressed is shown as an image. In particular, in the Doppler mode, a difference between a frequency of an ultrasonic signal transmitted at a pulse repetition frequency (PRF) from a probe (hereinafter referred to as a transmission frequency) and a frequency of a Doppler signal that is reflected by a moving target object and is received by the probe (hereinafter referred to as a reception frequency) is used. In other words, an image of a Doppler mode is formed by using a characteristic whereby a frequency of a Doppler signal from a target object that is approaching a probe is higher than the transmission frequency, and a frequency of a Doppler signal from a target object that is moving away from a probe is lower than the reception frequency.

For example, an ensemble may include the number of ultrasonic waves which are repeatedly transmitted to an identical position of a target object, in order to obtain at least one of color image lines forming an ultrasound image. In other words, a group of ultrasonic waves that are repeatedly transmitted to an identical position of a target object may be formed as an ensemble. Also, the ultrasound image may be obtained by aggregating a plurality of color image lines.

One of important factors in tissue Doppler imaging (TDI) is a frame rate. In order to have a faster frame rate, four or less ensembles are typically used in TDI. A frame rate is increased by about 20% or more each time an ensemble is reduced, and thus TDI is to be conducted by using a smaller number of ensembles.

Figure 1:
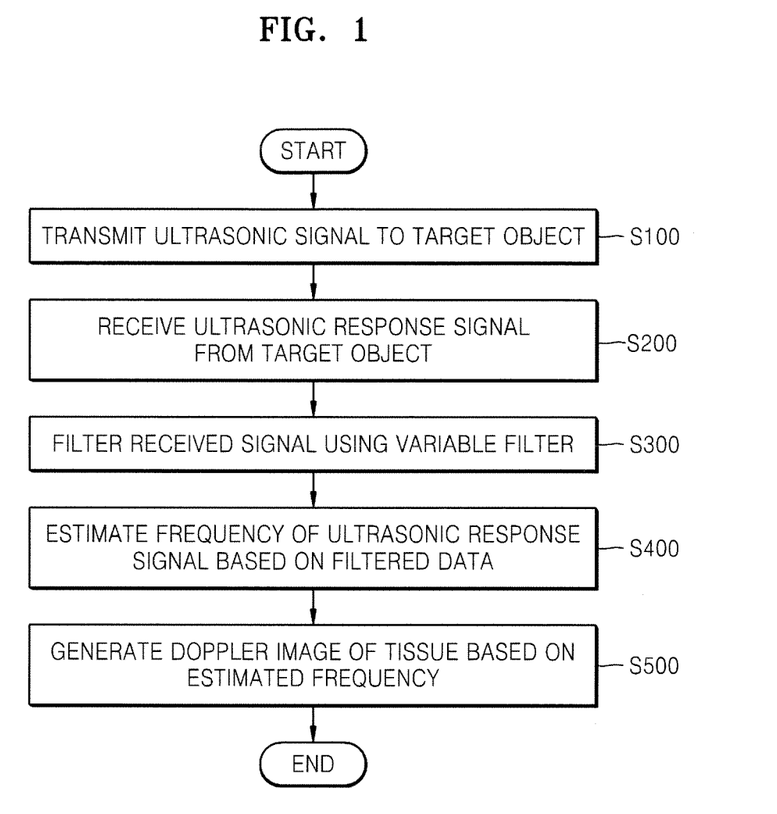
FIG. 1 is a flowchart illustrating a method of obtaining a Doppler image of tissue captured using an ultrasonic wave, according to an embodiment of the present invention.

FIG. 1 is a flowchart illustrating a method of obtaining a Doppler image of tissue captured using an ultrasonic wave, according to an embodiment of the present invention.

According to the method of obtaining a Doppler image of tissue captured using an ultrasonic wave of the current embodiment of the present invention, an ultrasonic signal is transmitted to a target object such that a plurality of ensembles are formed in operation S100, an ultrasonic response signal from the target object is received in operation S200, and the received ultrasonic response signal is filtered using a variable filter in operation S300. Also, according to the method, a frequency of the received ultrasonic response signal is estimated based on filtered data in operation S400, and a Doppler image of a tissue is generated based on the estimated frequency in operation S500.

The plurality of ensembles according to the current embodiment of the present invention may be at least two ensembles. The plurality of ensembles may preferably be two ensembles.

Operation S300 of filtering the received ultrasonic response signal using a variable filter may include obtaining at least one of data about an amplitude of the filtered received ultrasonic response signal and data about a phase of the filtered received ultrasonic response signal.

The variable filter according to the current embodiment of the present invention may include a filter that removes a portion of a direct current (DC) component from the received ultrasonic response signal.

Figure 2A:
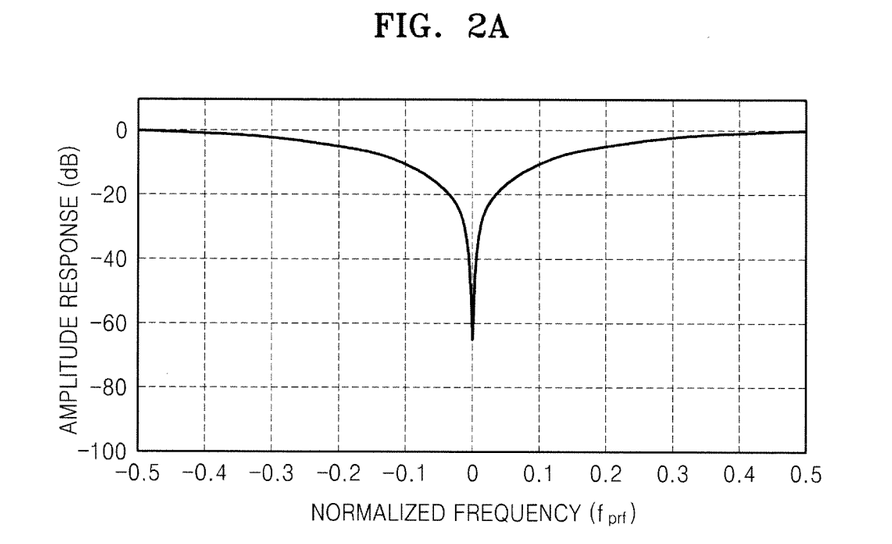
FIG. 2A illustrates an example of a frequency amplitude response of a direct current (DC) removal filter according to the conventional art.
Figure 2B:
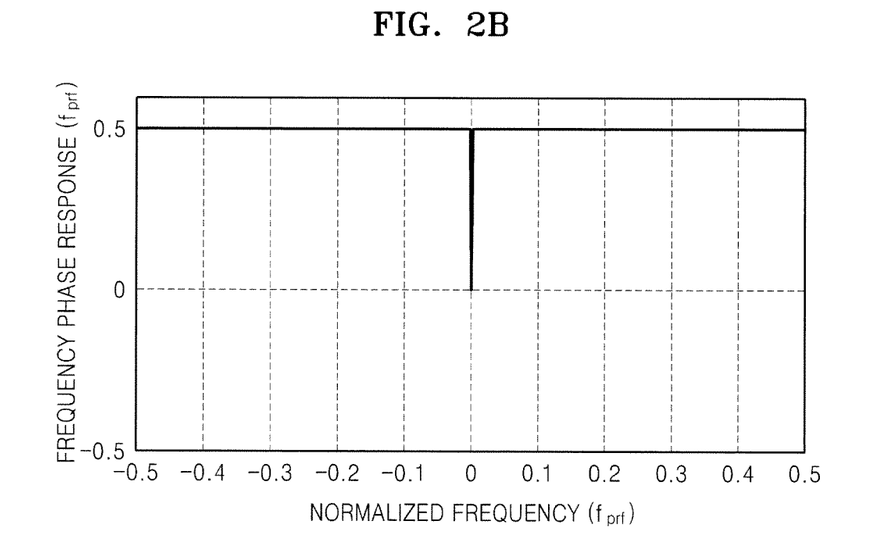
FIG. 2B illustrates an example of a frequency phase response of a DC removal filter according to the conventional art.
Figure 2C:
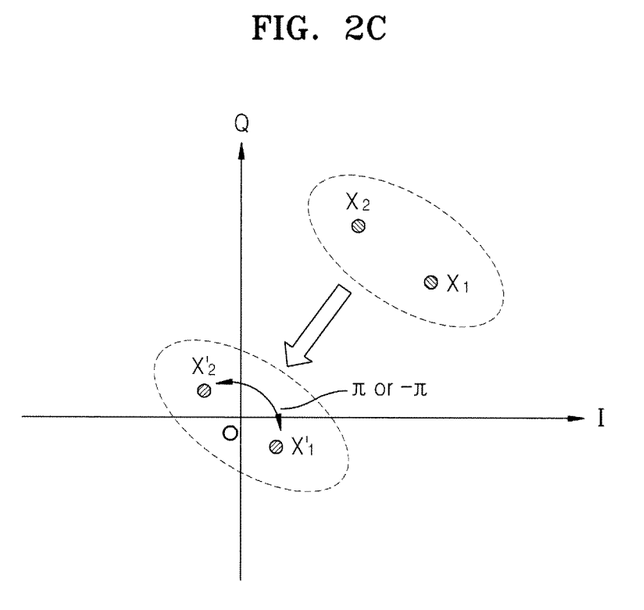
FIG. 2C illustrates an example of a variation of an ensemble signal after passing through a DC removal filter according to the conventional art.

FIG. 2A illustrates an example of a frequency amplitude response of a DC removal filter according to the conventional art. FIG. 2B illustrates an example of a frequency phase response of a DC removal filter according to the conventional art. FIG. 2C illustrates an example of a variation of an ensemble signal after passing through a DC removal filter according to the conventional art.

For convenience of description, an ensemble signal [x1 x2] is assumed as below. In general, when there are two ensembles, a DC removal filter according to the conventional art may be implemented in the form of a matrix as shown below.

$$\text{DC removal filter} = \begin{bmatrix} 0.5 & -0.5 \\ -0.5 & 0.5 \end{bmatrix}$$

The DC removal filter as described above may be obtained using a difference between a $$\text{bypass filter} \begin{bmatrix} 1 & 0 \\ 0 & 1 \end{bmatrix}$$

and a $$\text{mean filter} \begin{bmatrix} 0.5 & 0.5 \\ 0.5 & 0.5 \end{bmatrix},$$

which may be used as a low-band pass-filter. That is, the DC removal filter according to the conventional art may be expressed as below:

DC removal filter =

$$\text{Bypass filter} - \text{Mean filter} = \begin{bmatrix} 1 & 0 \\ 0 & 1 \end{bmatrix} - \begin{bmatrix} 0.5 & 0.5 \\ 0.5 & 0.5 \end{bmatrix} = \begin{bmatrix} 0.5 & 0.5 \\ -0.5 & 0.5 \end{bmatrix}$$

A frequency amplitude response and a frequency phase response with respect to the DC removal filter are illustrated in FIGS. 2A and 2B. A frequency response may be used when generating an ultrasonic image from which a DC component is removed. However, as illustrated in FIG. 2B, when the DC removal filter as described above is used, an ensemble signal (x1, x2) before filtering is changed into an ensemble signal (x1', x2') whose phase is always different from the ensemble signal before filtering by 180 degrees, and thus is not appropriate for TDI whose purpose is to represent velocities of tissues.

In regard to this, a variable filter as below may be included according to an embodiment of the present invention.

Variable filter =

$$\text{Bypass filter} - a^* \text{ Mean filter } (0 < a < 1) = \begin{bmatrix} 1 & 0 \\ 0 & 1 \end{bmatrix} - a^* \begin{bmatrix} 0.5 & 0.5 \\ 0.5 & 0.5 \end{bmatrix} = \begin{bmatrix} 1 - 0.5a & -0.5a \\ -0.5a & 1 - 0.5a \end{bmatrix}$$

According to an embodiment of the present invention, when the received ultrasonic response signal is filtered using the variable filter as described above, a signal from which a portion of a DC component is removed from the received ultrasonic response signal may be obtained.

Figure 3A:
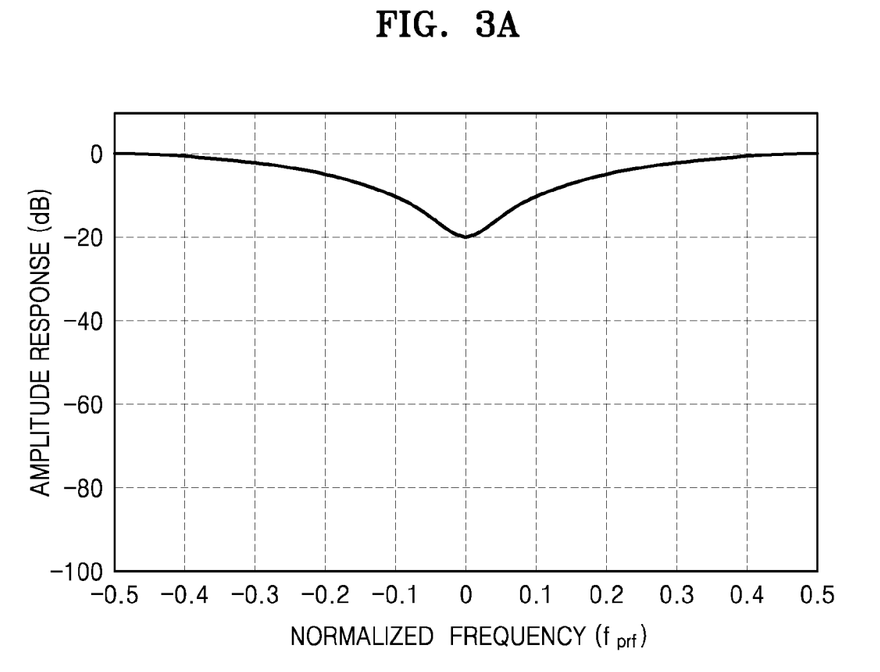
FIG. 3A illustrates an example of a frequency amplitude response of a DC removal filter according to an embodiment of the present invention.
Figure 3B:
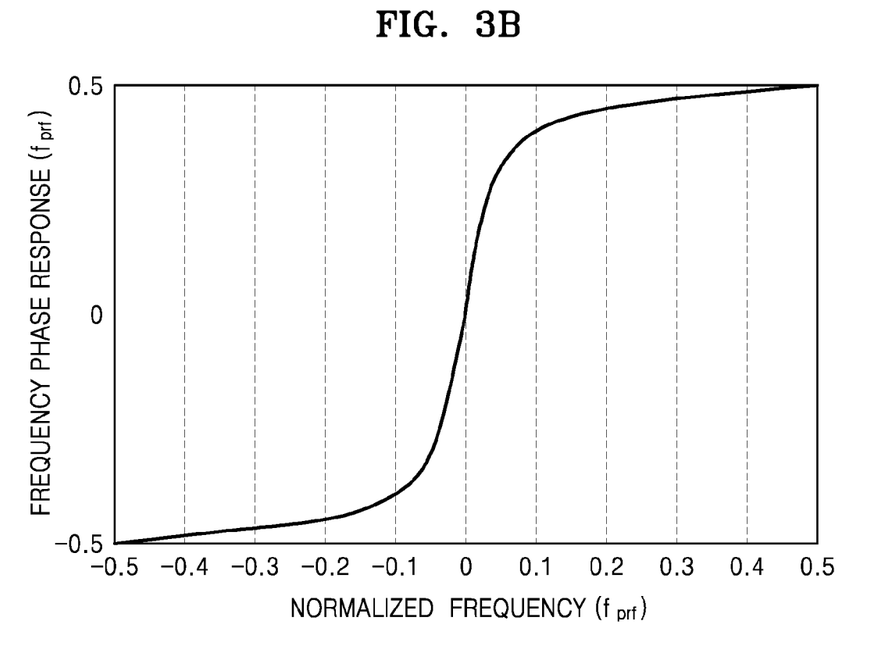
FIG. 3B illustrates an example of a frequency phase response of a DC removal filter according to an embodiment of the present invention.

FIG. 3A illustrates an example of a frequency amplitude response of a DC removal filter according to an embodiment of the present invention. FIG. 3B illustrates an example of a frequency phase response of a DC removal filter according to an embodiment of the present invention.

For example, when a=0.05, an amplitude response and a phase response of a variable filter according to an embodiment of the present invention are as illustrated in FIGS. 3A and 3B. That is, when a=0.05, a DC gain of the variable filter is −20 dB, and thus the variable filter does not completely remove a DC component. However, although values of the phase response of the variable filter vary due to distortion as illustrated in FIG. 3B, the phase response of the variable filter may have a monotonous increase curve and corresponds in almost a one-to-one correspondence to a normalized frequency (including input frequencies).

Figure 4:
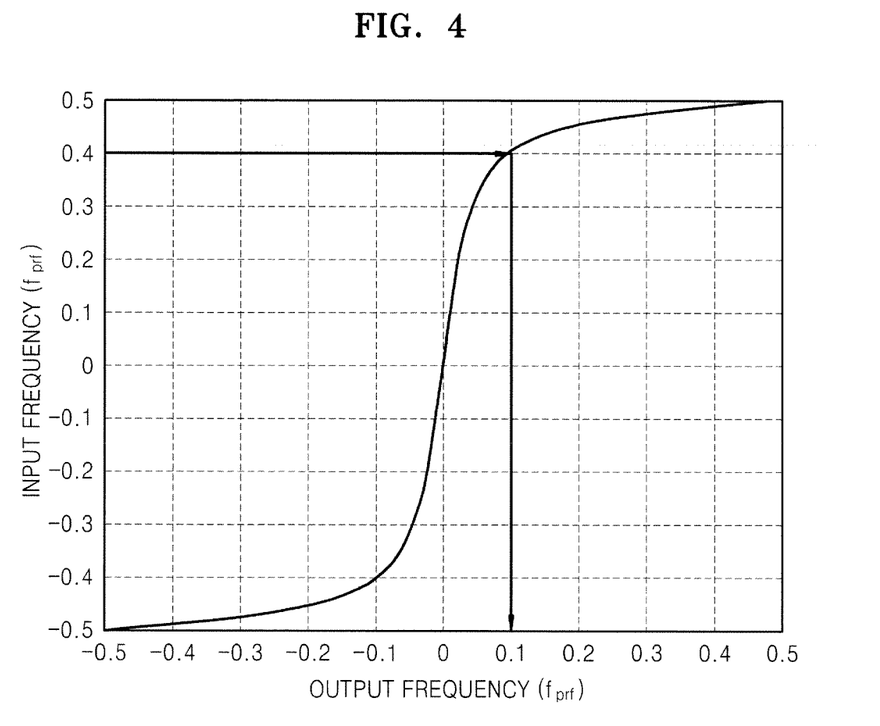
FIG. 4 illustrates an example of frequency estimation according to an embodiment of the present invention.

FIG. 4 illustrates an example of frequency estimation according to an embodiment of the present invention.

Operation S400 of estimating a frequency of a received ultrasonic response signal according to an embodiment of the present invention may further include obtaining a frequency phase response curve of a variable filter and correcting data about the filtered phase by using a value on the frequency phase response curve of the variable filter corresponding to the data about the filtered phase.

According to the current embodiment of the present invention, a response phase response curve of the variable filter as illustrated in FIG. 3B may be obtained. Referring to the phase response curve, when a signal corresponding to an ultrasonic wave whose original velocity is 0.1 prf passes through a variable filter, the filtered signal may be overestimated by about 0.4 prf.

According to the current embodiment of the present invention, data about the filtered phase on the frequency phase response curve (e.g., 0.4 prf) is corrected to a corresponding value (e.g., 0.1 prf), and thus an original frequency of the ultrasonic response signal may be relatively accurately estimated.

Operation S500 of generating a Doppler image of tissue based on the estimated frequency of the ultrasonic response signal may include obtaining an amplitude of the received ultrasonic response signal and generating a Doppler image of the tissue based on the obtained amplitude.

An image of a target object may be obtained based on the amplitude of the received ultrasonic response signal and the estimated frequency in a similar manner to the conventional art. Also, post-processing such as operations for improved color displaying (e.g., flash rejection) may be performed on the obtained image to obtain a high resolution image.

Figure 5:
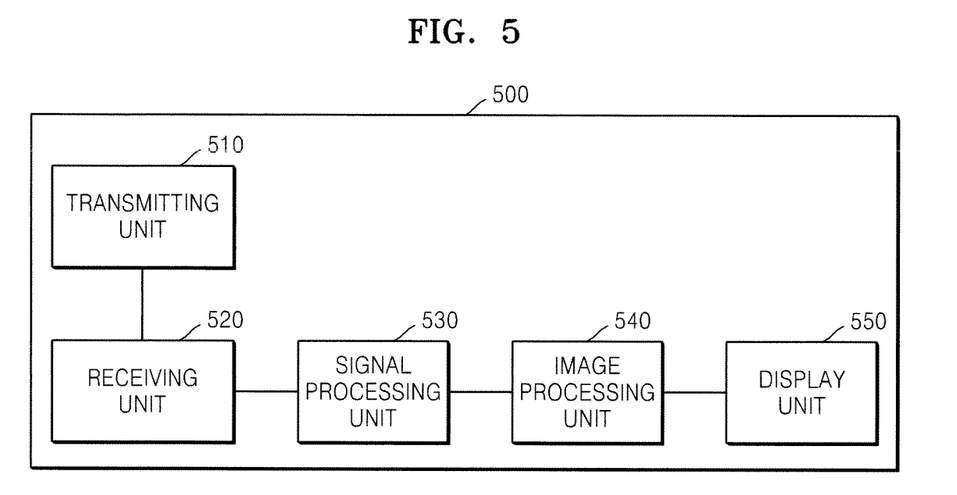
FIG. 5 illustrates an apparatus for obtaining a Doppler image of tissue, which is captured using an ultrasonic wave according to an embodiment of the present invention.

FIG. 5 illustrates an apparatus 500 for obtaining Doppler images of tissue, which are captured using an ultrasonic wave according to an embodiment of the present invention. Descriptions of the method provided above may be applied to the apparatus 500.

The apparatus 500 may include a transmitting unit 510 transmitting an ultrasonic signal to a target object such that a plurality of ensembles are formed, a to receiving unit 520 receiving a ultrasonic response signal from the target object, a signal processing unit 530 processing the received ultrasonic response signal, an image processing unit 540 generating a Doppler image of tissue using the processed ultrasonic response signal, and a display unit 550 displaying the Doppler image of tissue.

The plurality of ensembles according to the current embodiment of the present invention may be at least two ensembles. The plurality of ensembles may preferably be two ensembles.

The apparatus 500 may further include a probe (not shown) that is connected to the transmitting unit 510 and the receiving unit 520 to transmit or receive an ultrasonic signal. Also, the apparatus 500 may include a beamformer (not shown) that is connected between the transmitting unit 510 and the receiving unit 520 and the signal processing unit 530 to perform transmission focusing and reception focusing of the ultrasonic signal.

The transmitting unit 510 may transmit the ultrasonic signal at a pulse repetition frequency (PRF) to obtain a Doppler mode image regarding an observation area of a target object.

Figure 6:
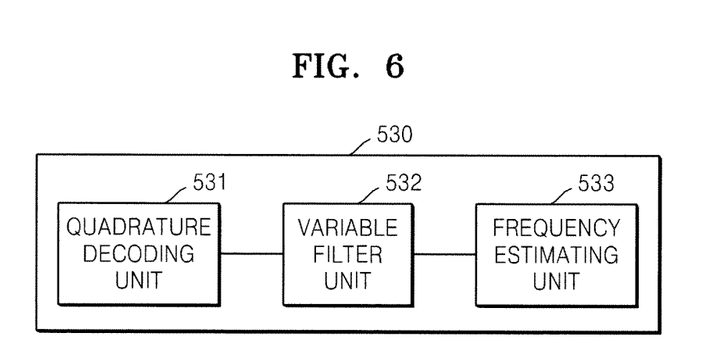
FIG. 6 illustrates a signal processing unit according to an embodiment of the present invention.

FIG. 6 illustrates the signal processing unit 530 according to an embodiment of the present invention.

The signal processing unit 530 may include a variable filter unit 532 filtering a received ultrasonic response signal and a frequency estimating unit 533 estimating a frequency of the received ultrasonic response signal based on the filtered data.

The variable filter unit 532 may include a filter for removing a portion of a DC component from the received ultrasonic response signal. The variable filter unit 532 may obtain data about an amplitude of the filtered received ultrasonic response signal and data about a phase of the filtered received ultrasonic response signal.

Also, the signal processing unit 530 may further include a quadrature decoding unit 531. The quadrature decoding unit 530 may decode a Doppler signal into an I signal formed of an in-phase component and a Q signal formed of a quadrature component.

Figure 7:
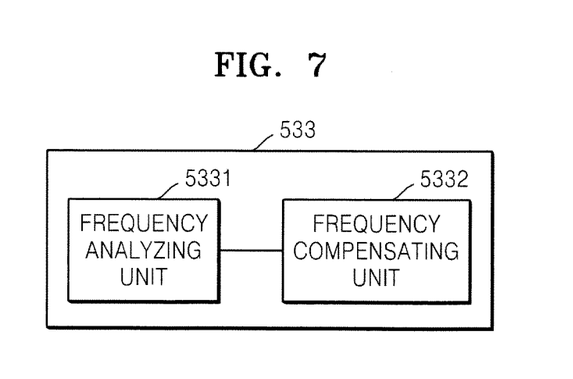
FIG. 7 illustrates a frequency estimating unit according to an embodiment of the present invention.

FIG. 7 illustrates the frequency estimating unit 533 according to an embodiment of the present invention.

The frequency estimating unit 533 may include a frequency analyzing unit 5331 and a frequency compensating unit 5332.

The frequency analyzing unit 5331 may obtain a frequency phase response curve from the variable filter unit 532. The frequency compensating unit 5332 may compensate for data about the phase of the filtered ultrasonic response signal by using the obtained frequency phase response curve from the variable filter unit 532. Also, the frequency compensating unit 5332 may correct data about the filtered phase of the ultrasonic response signal by using a value on the frequency phase response curve from the variable filter unit 532 corresponding to the data about the filtered phase of the ultrasonic response signal.

Figure 8:
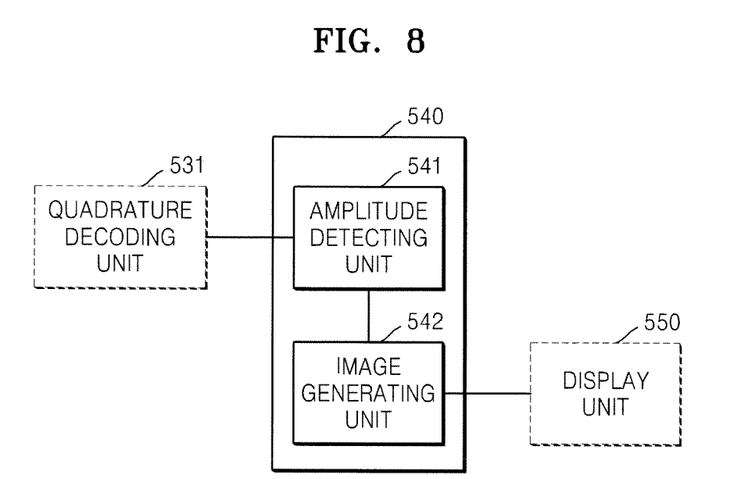
FIG. 8 illustrates an image processing unit according to an embodiment of the present invention.

FIG. 8 illustrates the image processing unit 540 according to an embodiment of the present invention.

The image processing unit 540 may include an amplitude detecting unit 541 and an image generating unit 542.

The amplitude detecting unit 541 may be connected to the quadrature decoding unit 531 to obtain an amplitude of a received ultrasonic response signal.

The image generating unit 542 is connected to a display unit 550 and may generate a Doppler image of tissue, based on the estimated frequency and the obtained amplitude.

In other words, the image generating unit 542 may obtain an image of the target object in a similar manner as in the conventional art based on the amplitude and the estimated frequency of the received ultrasonic response signal. Also, post-processing such as operations for improved color displaying (e.g., flash rejection) may be performed to the obtained image, thereby obtaining a high resolution image.

The embodiments of the present invention can be written as computer programs and can be implemented in general-use digital computers that execute the programs using a computer readable recording medium.

Examples of the computer readable recording medium include read-only memory (ROM), random-access memory (RAM), CD-ROMs, magnetic tapes, floppy disks, optical data storage devices, etc. (e.g., transmission through the Internet).

While this invention has been particularly shown and described with reference to preferred embodiments thereof, it will be understood by those of ordinary skill in the art that various changes in form and details may be made therein without departing from the spirit and scope of the invention as defined by the appended claims. The preferred embodiments should be considered in a descriptive sense only and not for purposes of limitation. Therefore, the scope of the invention is defined not by the detailed description of the invention but by the appended claims, and all differences within the scope will be construed as being included in the present invention.

What is claimed is:

1. A method of obtaining a Doppler image of tissue, which is captured using an ultrasonic wave, the method comprising:
    transmitting an ultrasonic signal to a target object such that two ensembles are formed;
    receiving an ultrasonic response signal from the target object;
    filtering the received ultrasonic response signal by using a variable filter;
    obtaining data about a filtered phase of the received ultrasonic response signal;
    correcting the data about a filtered phase by using a value on a frequency phase response curve of the variable filter corresponding to the data about a filtered phase;
    estimating a frequency of the received ultrasonic response signal based on the corrected data about a filtered phase; and
    generating the Doppler image of the tissue based on the estimated frequency,
    wherein the variable filter variably decreases an amplitude of a direct current (DC) component from the received ultrasonic response signal.

2. The method of claim 1, further comprising obtaining data about a filtered amplitude of the received ultrasonic response signal.

3. The method of claim 2, wherein the generating of the Doppler image of the tissue based on the estimated frequency comprises:
    obtaining an amplitude of the received ultrasonic response signal; and
    generating the Doppler image of the tissue based on the estimated frequency and the obtained amplitude.

4. A non-transitory computer readable recording medium having embodied thereon a program for executing the method of one of claims 1, 2, and 3.

5. An apparatus for obtaining a Doppler image of tissue, which is captured using an ultrasonic signal, the apparatus comprising:
    a transmitter configured to transmit an ultrasonic signal to a target object such that two ensembles are formed;
    a receiver configured to receive an ultrasonic response signal from the target object;
    a signal processor configured to process the received ultrasonic response signal; and
    an image processor configured to generate the Doppler image of the tissue using the processed ultrasonic response signal,
    wherein the signal processor comprises:
        a variable filter configured to filter the received ultrasonic response signal and obtain data about a filtered phase of the received ultrasonic response signal; and
        a frequency estimator configured to correct the data about a filtered phase by using a value on a frequency phase response curve of the variable filter corresponding to the data about a filtered phase and estimate a frequency of the received ultrasonic response signal based on the corrected data about a filtered phase, and
    wherein the variable filter variably decreases an amplitude of a direct current (DC) component from the received ultrasonic response signal.

6. The apparatus of claim 5, wherein the variable filter obtains data about a filtered amplitude of the received ultrasonic response signal.

7. The apparatus of claim 6, wherein the image processor comprises:
    an amplitude detector configured to obtain an amplitude of the received ultrasonic response signal; and
    an image generator configured to generate the Doppler image of the tissue based on the estimated frequency and the obtained amplitude.

* * * * *